United States Patent
Miyajima et al.

[11] Patent Number: 5,943,706
[45] Date of Patent: Aug. 31, 1999

[54] HELMET

[75] Inventors: Iwao Miyajima, Niiza; Hideshi Kitahara, Kawaguchi, both of Japan

[73] Assignee: TS Tech Co., Ltd., Japan

[21] Appl. No.: 09/043,533

[22] PCT Filed: Jul. 25, 1997

[86] PCT No.: PCT/JP97/02589

§ 371 Date: Mar. 20, 1998

§ 102(e) Date: Mar. 20, 1998

[87] PCT Pub. No.: WO98/04164

PCT Pub. Date: May 2, 1998

[30] Foreign Application Priority Data

Jul. 26, 1996 [JP] Japan .................................. 8-215150
Jul. 24, 1997 [JP] Japan .................................. 9-212680

[51] Int. Cl.$^6$ .......................................................... A42B 3/12
[52] U.S. Cl. ............................................... 2/412; 2/425
[58] Field of Search .................................. 2/412, 410, 411, 2/414, 425

[56] References Cited

FOREIGN PATENT DOCUMENTS

| 60-81307 | 5/1985 | Japan . |
|---|---|---|
| 63-282303 | 11/1988 | Japan . |
| 5-295607 | 11/1993 | Japan . |
| 9-176908 | 7/1997 | Japan . |

Primary Examiner—Diana L. Oleksa
Attorney, Agent, or Firm—Lorusso & Loud

[57] ABSTRACT

The present invention concerns a helmet including a shell formed from a thermoplastic resin, for example, by blow molding or injection molding, and a shock absorbing liner disposed on the inside of the shell. The shock absorbing liner is formed of polyvinylidene chloride foam. By forming the shock absorbing liner of polyvinylidene chloride foam, it is possible to provide a helmet having less temperature dependent change in compression strength upon molding, excellent shock adsorption and restorability, excellent impact shock adsorbing performance upon a second hit on one identical portion and excellent dimensional accuracy in manufacture.

3 Claims, 11 Drawing Sheets

| Item | Polyvinylidene chloride (blowing factor 36) | Foamed styrol (blowing factor 33) |
|---|---|---|
| Density　　　$kg/m^3$ | 40 | 30 |
| Compression strength　　$kg/m^2$ (5% strain) | 2.0 | 1.8 |
| Bending strength $kg/cm^2$ | 7.0 | 5.0 |
| Heat conductivity (average temperature 0°C)　　$kcal/mh°C$ | 0.019 | 0.028 |
| Water absorption $g/100cm^2$ | less than 0.005 | less than 0.005 |
| Moisture permeability　　$g/mh\ mmHg$ | $2 \times 10^{-3}$ | $10 \times 10^{-4}$ |
| Combustibility | Self extinguishability | Self extinguishability (FR agent used) |

Fig. 8

|  | Density | Permanent compression strain ratio (JISK6767) | 10% compression strength (Kg/cm³) | | |
|---|---|---|---|---|---|
|  |  |  | -10°C | 23°C | 50°C |
| PVDC foams | 40 Kg/m³ | 7 % | 3.0 | 2.5 | 2.2 |
| PS foams | 40 Kg/m³ | 18 % | 4.5 | 3.0 | 2.2 |
| PP foams | 40 Kg/m³ | 8 % | 6.2 | 2.4 | 1.6 |

Fig. 9

Dropping height of a striker for impact shock absorbing
test and number of cycle of impact shock

| Type of safety caps | | Type A | Type B | Type C |
|---|---|---|---|---|
| dropping height cm | Planer type steel anvil | 1 6 0 | 1 7 0 | 1 8 3 |
| | Semi-spherical steel anvil | — | — | 1 3 8 |
| Number of cycles of impact shock applied on one identical impact shock points | | 1 | 2 | 2 |

HELMET

TECHNICAL FIELD

The present invention concerns a helmet and it particularly relates to a helmet which is worn as a safety cap for sport driving of a two wheeled vehicle or four wheeled vehicle and to such a helmet in which a shock absorbing liner is improved.

BACKGROUND ART

Heretofore, a helmet has a shell on an outer side and a shock absorbing liner disposed on the inside of the shell. As the shock absorbing liner, polystyrene (PS) foams, polypropylene (PP) foams and the like have been used but PS foams have a drawback in that they have poor restorability after releasing compression upon impact shock. Further, PP foams have a drawback of undergoing a large reduction in compression strength at high temperature.

Further, in helmets using thermoplastic resins for the shell members, it has been difficult in view of strength or the like to satisfy JIS class C standards due to the foregoing drawbacks of the shock absorbing liner. For satisfying the JIS class C standards, FRP of high strength is used as the shell material or the thickness of the liner is increased for coping with the foregoing problems.

The prior art use of FRP of high strength as the shell material or increase in the thickness of the liner, results in drawbacks in that the shape of the helmet is enlarged, the helmet is made heavy, production cost is increased or user's demand can not be satisfied in view of the design.

An object of the present invention is to provide a helmet showing less temperature dependent change of the compression strength, excellent impact absorption and restorability, excellent impact absorption upon second hitting on an identical portion and also excellent dimensional accuracy in manufacture.

Another object of the present invention is to provide a helmet having satisfactory compatibility between its shock absorbing liner and its shell and dimensional accuracy, without increasing the thickness of the shock absorbing liner and capable of easily satisfying user's demand in view of the design.

JIS class C standard will be explained here. Helmets are specifically defined in "Protective Helmets for Vehicular Users" of Japanese Industrial Standards (JIS-T 8133). Such helmets are classified in three types: A, B, C in which A is directed to a vehicle having an exhaust capacity of 125 cc or less, B is directed to two-wheeled automobiles according to road regulations in Japan and C concerns helmets for racing, as well as B. Regarding C, it is specified in (a) that an impact acceleration of 2945 m/s$^2$ (300, 3 G) is prevented, and (b) duration time is 4 ms or less upon an impact shock acceleration of 1475 m/s$^2$ (150, 4 G) or higher.

Figure 9:
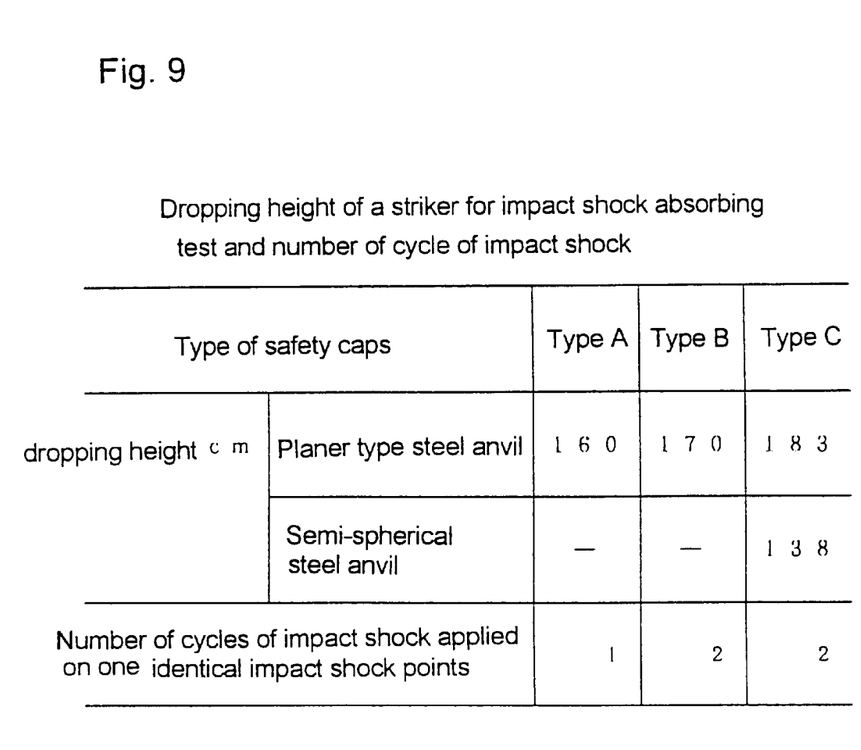
FIG. 9 is a table of dropping heights and the number of cycles of impact shocks of a striker for impact shock absorbing test.

In the measurement of the impact acceleration, a striker for an impact absorbing test is dropped without vibrations from the height shown in FIG. 9 and impact shock transmitted by way of a safety cap when a predetermined impact point of a specimen collides against a steel anvil is measured by an acceleration gage and a measuring recording device connected therewith, to examine whether or not the value satisfies the above-mentioned numerical standard.

Measuring conditions and the like are according to FIG. 9 and the following descriptions.

While the steel anvils used in the test inspection are different depending on the type of the safety cap as shown in FIG. 9 and, in the class C safety cap, planer type steel anvils are used at two positions and semi-spherical steel anvils are used at the other two positions of the four impact points of the safety cap.

Figure 10:
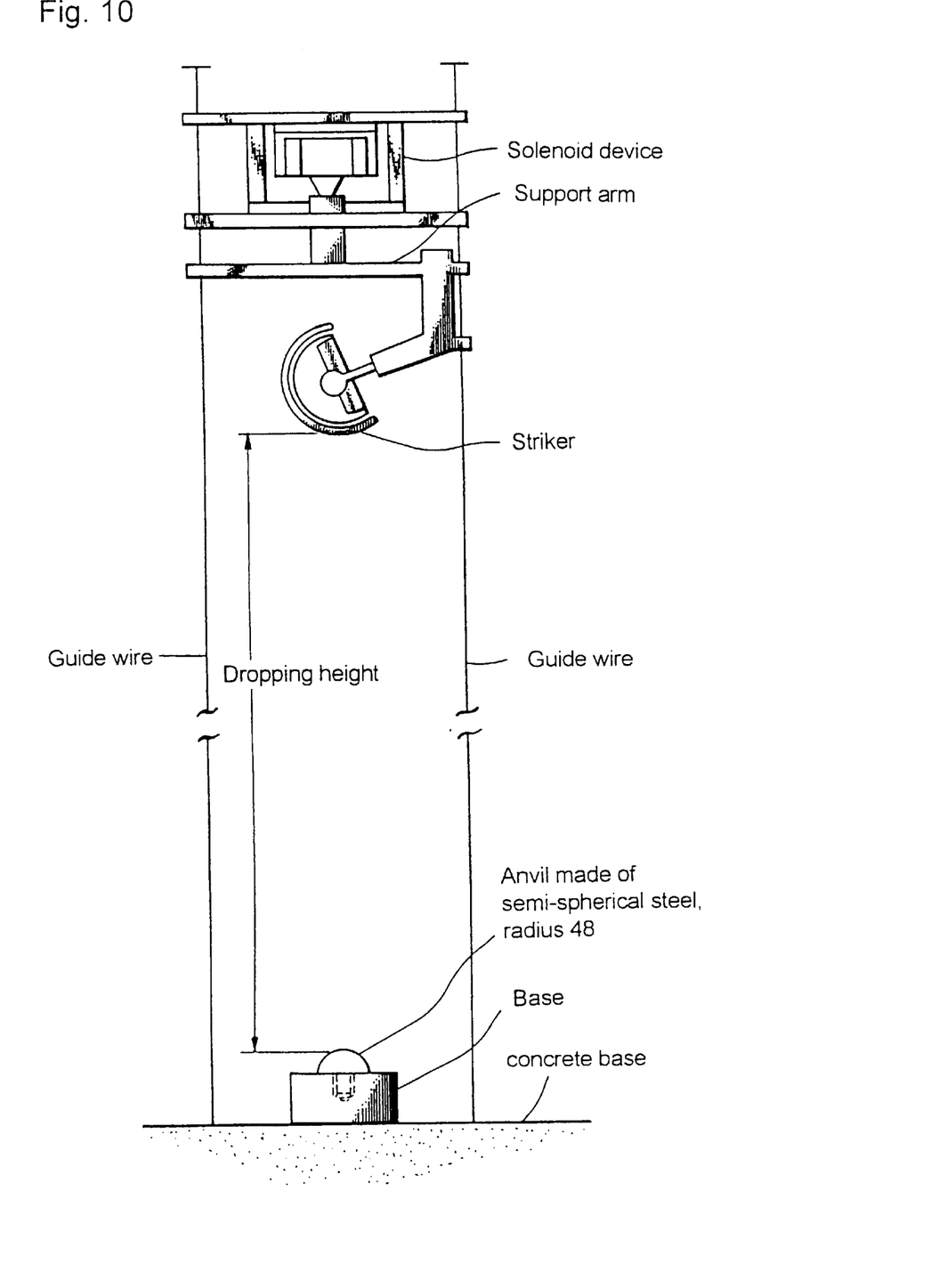
FIG. 10 is a schematic view of an impact shock absorbing test device.
Figure 12:
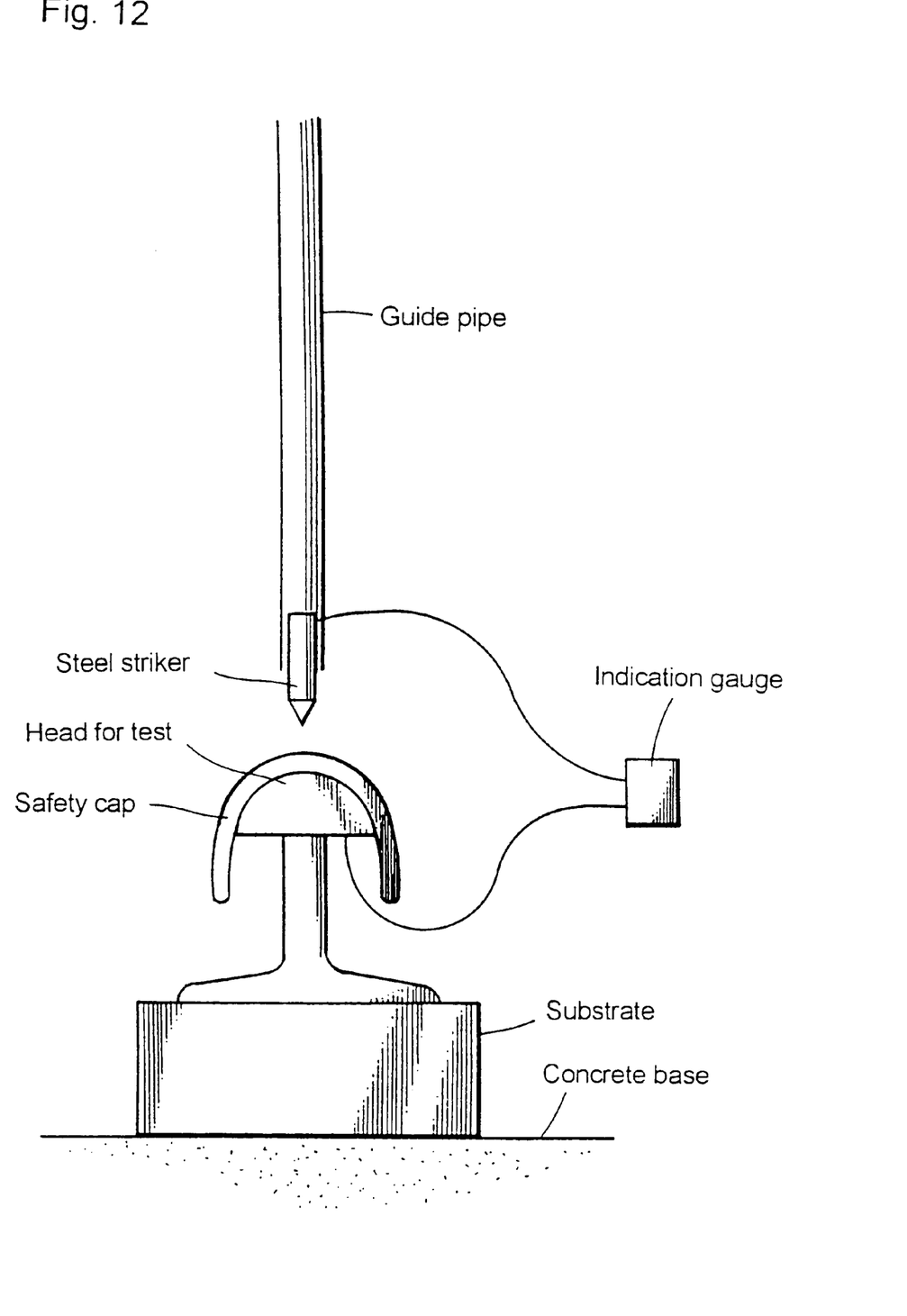

In class B and class C safety caps, the test range is defined as a portion above a head. However, a portion within 50 mm from the edge of the cap body is excluded. The impact shock points are determined at four optional positions within the test range, and the distance between each of the impact shock points is defined as ⅕ or greater for the maximum circumference of the safety cap. Further, the number of impact shocks applied on one identical impact shock point is as shown in FIG. 9. An outline of a testing device is shown in FIG. 10 to FIG. 12.

DISCLOSURE OF THE INVENTION

A helmet according to the present invention has a shell formed by injection molding of a thermoplastic resin and an impact shock absorption liner disposed on the inside of the shell, wherein the liner is formed of polyvinylidene chloride foam.

In this case, the liner comprising polyvinylidene chloride foam suitably has a two layered structure comprising a less foamable polyvinylidene chloride foam and a highly foamable polyvinylidene foam.

The present invention concerns a helmet H comprising a shell 10 and an impact shock absorbing liner 20 disposed on the inside of the shell 10, formed, for example, by blow molding or injection molding of a thermoplastic resin.

The impact shock absorbing liner 20 is formed of polyvinylidene chloride foam. The liner composed of the polyvinylidene chloride foam is suitably a dual layer structure of less a foaming polyvinylidene chloride foam 21 and a highly foamable polyvinylidene chloride foam 22.

As described above, by making the shock absorbing liner 20 of polyvinylidene chloride foam, it is possible to provide a helmet H showing a less temperature dependent change in compression strength during molding, excellent impact shock absorption and storability, and excellent impact shock absorption upon a second hit on same spot and also excellent dimensional accuracy in manufacture.

According to the present invention, since polyvinylidene chloride foam is used as the impact shock absorbing liner, distortion during molding is small so that a liner of high dimensional accuracy can be manufactured and, in addition, foaming gases scarcely escape from the foam, so that it is excellent in dimensional stability and performance stability for a long period of time.

Further, the temperature dependent change of the compression strength is small and the compression strength at high temperature is better maintained. Further, it has excellent restorability upon releasing compression and, in particular, it is excellent in impact shock absorption performance at +50° C., and impact shock absorption upon a second hit in the same spot and can sufficiently withstand second impact shock in the helmet in the impact shock test of JIS-T 8133 SNELL M95.

Accordingly, it is possible to provide a helmet showing less temperature dependent change of the compression strength, excellent impact shock absorption and restorability, excellent impact shock absorption performance upon second hit on the same location and excellent dimensional accuracy in manufacture, without increase in weight, increase of cost, increase in the thickness of the impact shock absorbing liner or the like.

Other advantages of the present invention will become apparent from the following description.

BRIEF EXPLANATION OF THE DRAWINGS

FIG. 11 is a schematic view of a striker used in the impact shock absorbing test and FIG. 12 is a schematic view of a penetration resistant test device.

BEST MODE FOR PRACTICING THE INVENTION

A preferred embodiment of the present invention will be explained with reference to the drawings. Members, arrangement, and the like to be explained do not restrict the present invention and can be modified variously within the scope of the present invention.

Figure 1:
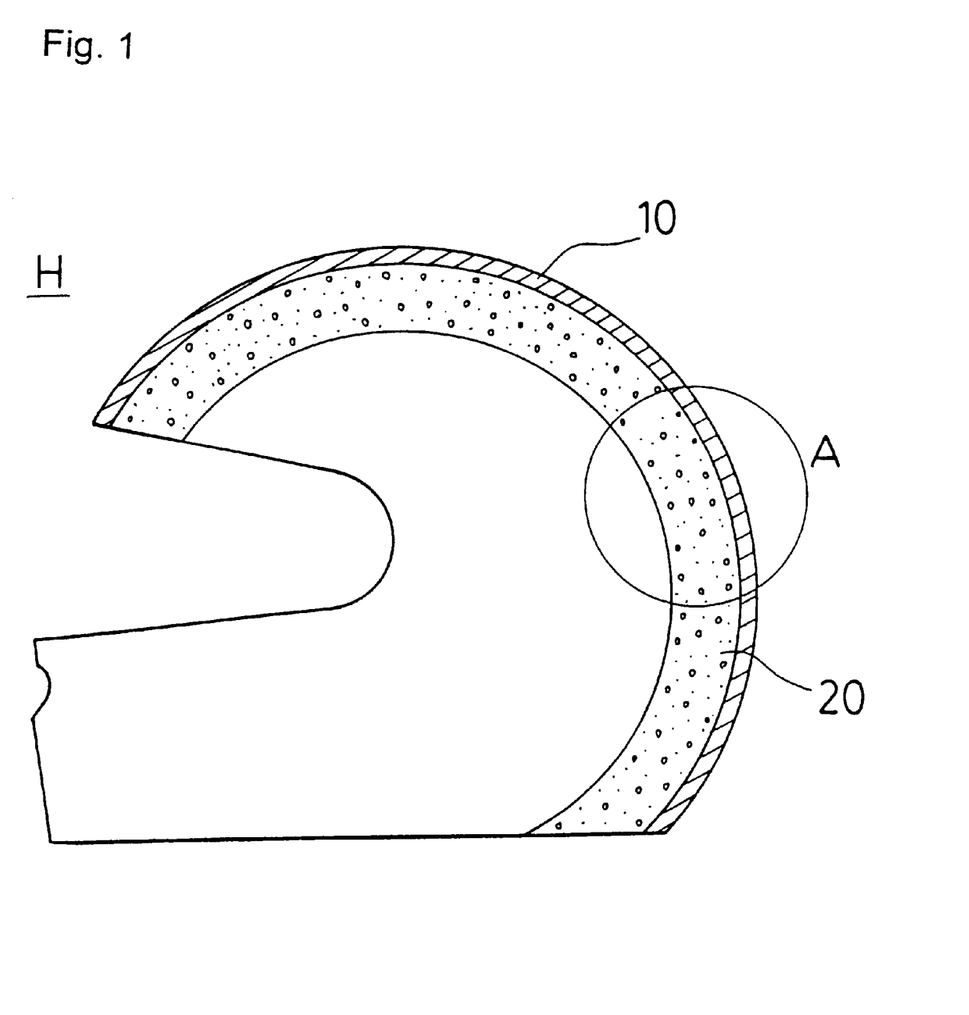
FIG. 1 is a schematic cross sectional view of a helmet according to the present invention.

As shown in FIG. 1, a helmet H of this embodiment is a full face type helmet in which a shell 10 forms the outside, and a shock absorbing liner 20 is disposed on the inside of the shell 10.

The shell 10 of this embodiment is formed into a predetermined shape from PP, ABS, PA or the like, which are thermoplastic resins, by injection molding, blow molding, or similar other molding.

Figure 2:
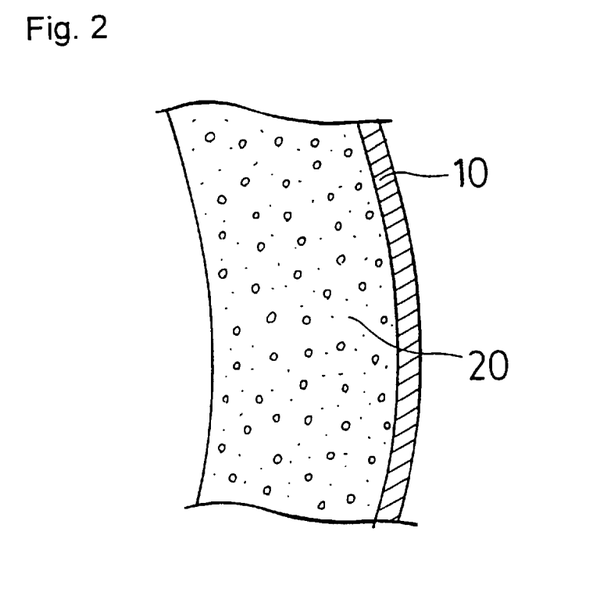
FIG. 2 is an enlarged cross sectional view for a portion A in FIG. 1.
Figure 2:
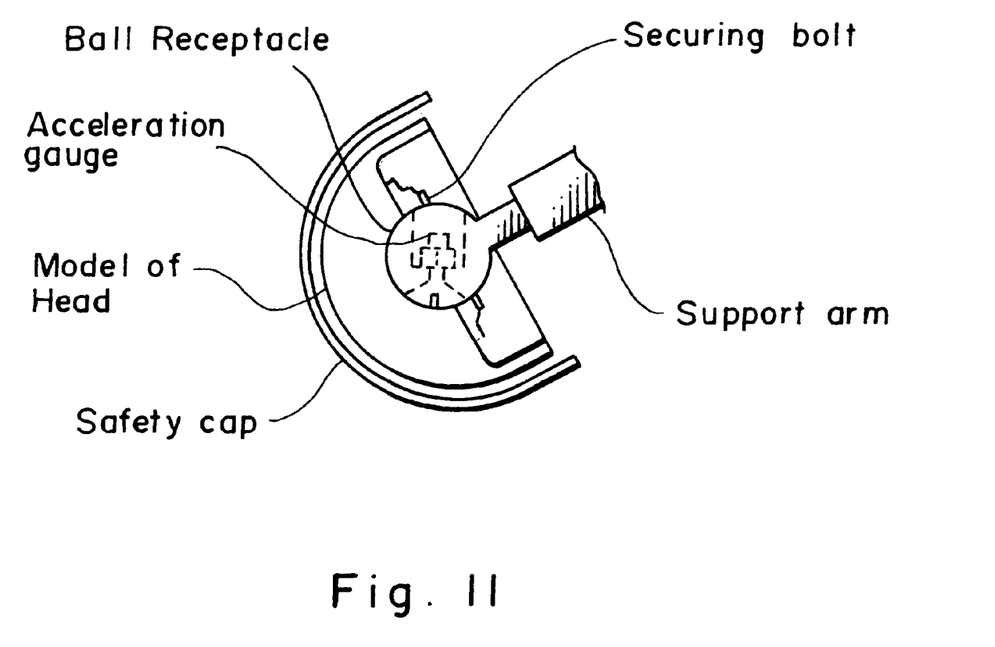

Then, the shock absorbing liner 20 is disposed on the inside of the shell 10. As shown in FIG. 1 and FIG. 2, the shock absorbing liner 20 in this embodiment is composed of a foam of a single density of polyvinylidene chloride (PVDC) and is formed to a predetermined thickness on the inside. The shock absorbing liner 20 used in this embodiment has a density of 60 g/l, or 0.06 g/cm$^3$ and can be manufactured by conventional blow molding. Then, the shock absorbing liner 20 is conformed to the inner shape of the shell 10 so as to fit to the inside of the shell 10.

The shock absorbing liner 20 of this embodiment is satisfactory in heat insulating performance and also satisfactory in gas barrier property. That is, polyvinylidene chloride foams show less reduction of compression strength upon heating at high temperature and have excellent restorability upon release of compression upon impact shock. In view of the above, it has better, as compared with foamed styrol, resistance to impact shock. The dimensional accuracy is 0.19% for polyvinylidene chloride foam according to the present invention, 0.3% for PS and 3–5% for PE or PP, so that polyvinylidene chloride foam produces more excellent dimensional accuracy in molding products as compared with the conventional materials used for the shock absorbing liner. Therefore, it is possible to conform it to the shell shape so as to be in intimate contact with various shapes of shells.

Figure 4:
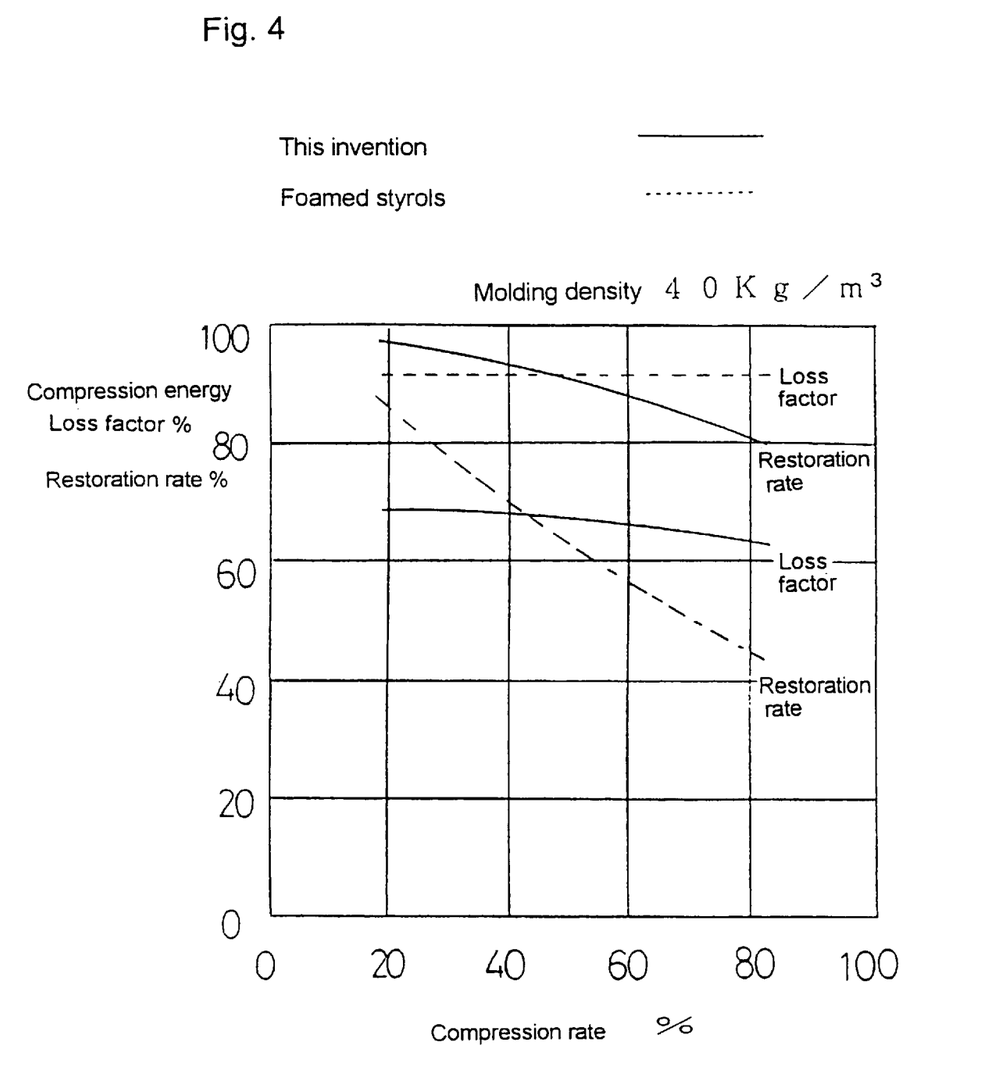
FIG. 4 is a graph showing restoration versus compression of an impact shock absorbing liner according to the present invention.

As described above, when the shock absorbing liner 20 is formed of a polyvinylidene chloride foam, the thickness can be remarkably reduced compared with foamed styrol or foamed PP. The shock absorbing liner 20 of this embodiment is suitable regarding the physical properties required for helmets and, as shown in FIG. 4 to FIG. 8, it has less temperature dependent change of the compression strength, excellent restorability, resistance to compression and bending and is flexible as well. As shown in FIG. 4, it is excellent in restorability or loss factor compared with foamed styrol.

Figure 5:
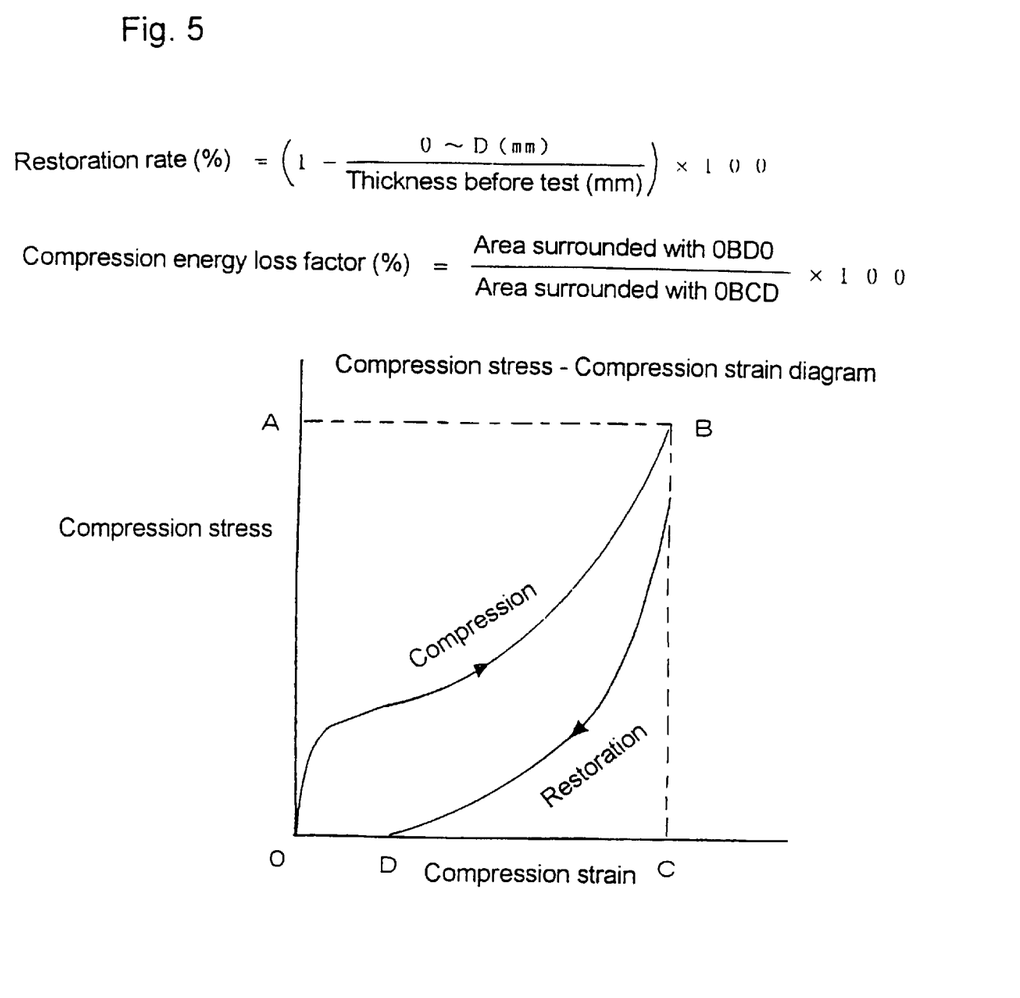
FIG. 5 is a diagram for a compression strength and a compression strain of an impact shock absorbing liner according to the present invention.

In FIG. 5, a test piece of 25 mm thickness and about 100 mm length was compressed at a rate of 10 mm/mm to 25%, 50% and the 75% of the original thickness of the test piece respectively, the load was instantly removed at an identical rate, and compression stress-compression strain graphs were recorded to obtain the restorability as shown in the figure.

Figure 6:
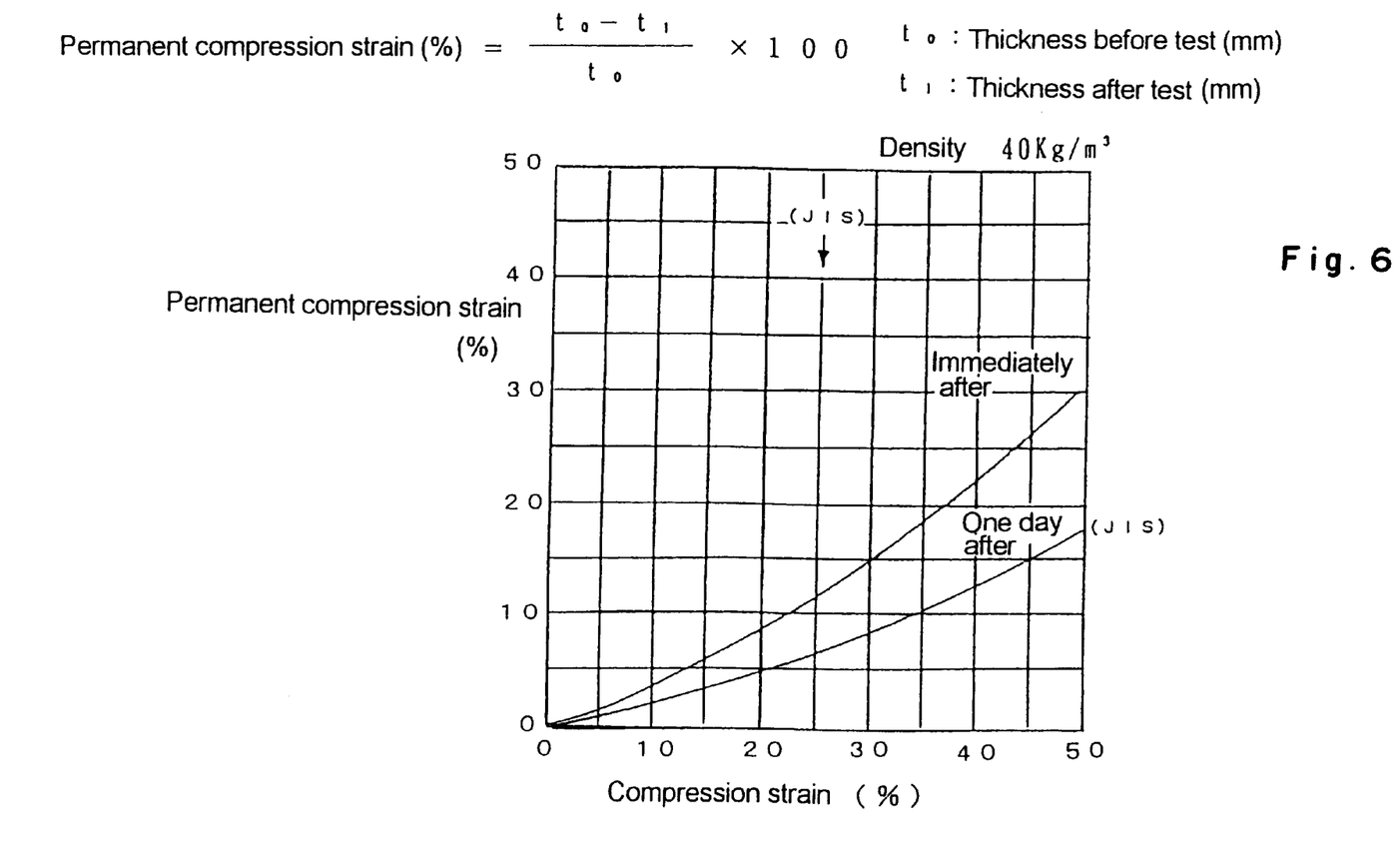
FIG. 6 is a diagram showing a permanent compression strain of an impact absorbing liner according to the present invention.

Further, as shown in FIG. 6, permanent compression strain was measured and calculated according to JIS K6767 specified in Japanese Industrial Standards as the test method for mechanical properties of foams. A test piece of 20 mm in thickness and about 50 mm in both length and width was put between two parallel flat plates (compression plates), fixed under compression to 10%, 25% and 50% of the original thickness of the test specimen, and left for 22 hours. Then the test piece was taken out of the flat plates and the thickness was measured immediately thereafter or after leaving at a room temperature of 23° C. for 24 hours and determined according to the equation shown in the figure.

Figure 7:
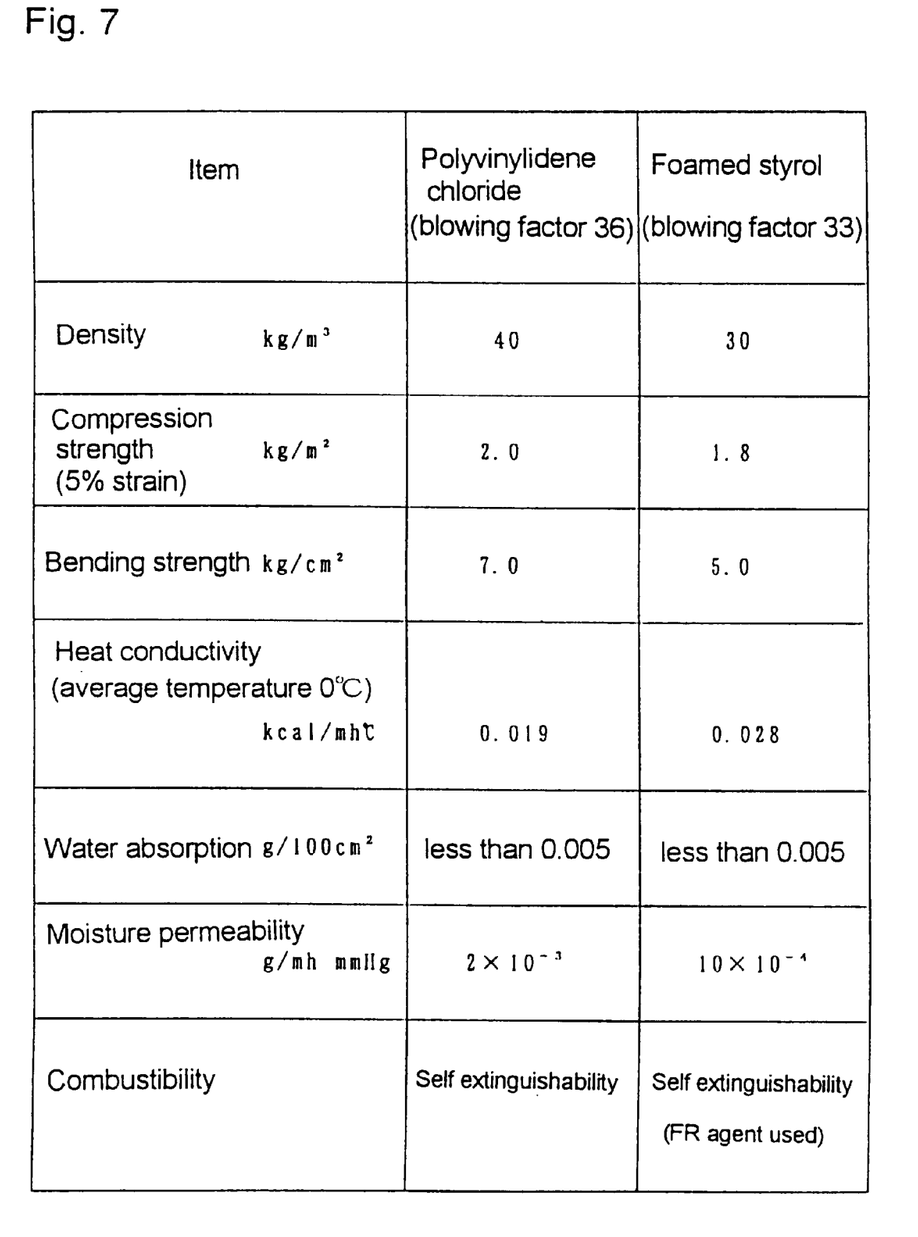
FIG. 7 is a chart for properties comparing polyvinylidene chloride foam used in this example in comparison with foamed styrol.
Figure 8:
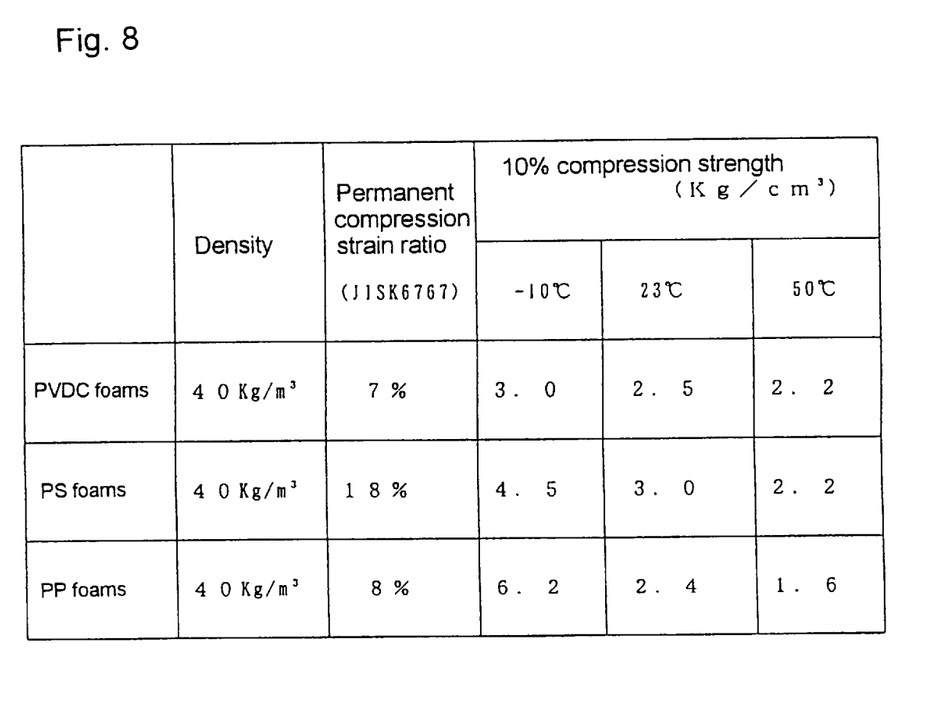
FIG. 8 is a comparison chart for the physical properties of PVDC foams, PS foams and PP foams.

FIG. 7 is a table for the physical properties of the polyvinylidene chloride foam used in this embodiment and foamed styrol, for comparison, and FIG. 8 is a table for the physical properties of PVCD foams, PS foams and PP foams for comparison. As shown in the figure, PS foams have a relatively lower temperature dependency such as 4.5 at −10° C. and 2.2 at 50° C. However, the compression permanent strain ratio is as high as 18%. Further, PP foams have the permanent compression strain ratio as small as 8% but the temperature dependence of the compression strength is as high as 6.2 at −10° C. and 1.6 at 50° C. On the contrary, polyvinylidene chloride foams (PVDC foams) show a permanent compression strain ratio of as small as 7% and, in addition, a lower temperature dependency as small as 3.0 at −10° C. and 2.2 at 50° C. compared with the conventional materials. Further, the heat conduction ratio is smaller compared with foamed styrols, and heat insulation is stable in a helmet subject to a large temperature difference between summer and winter seasons.

Figure 3:
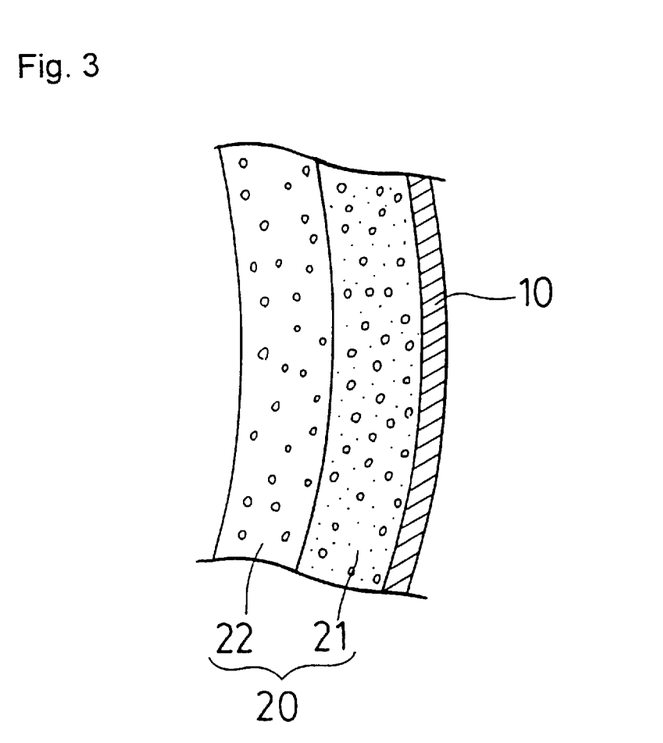
FIG. 3 is an enlarged cross sectional view similar to FIG. 2 showing another embodiment.

FIG. 3 shows another embodiment of the present invention, which is an enlarged cross sectional view similar to FIG. 2. This embodiment shows an example in which the shock absorbing liner has two layers, with a less foaming (high density) layer 21 being in contact with shell 10 while a highly foaming (low density) layer 22 being formed for the inside (head). The less foaming layer 21 and the highly foaming layer 22 are joined, for example, with an adhesive. As described above, PS foams are sensitive to second impact shock, and PP foams have temperature dependence. Therefore, the shock absorbing liner has dual-layers of polyvinylidene chloride foams (PVCD foams), in which the less foaming (high density) layer 21 is formed on the shell 10 and a highly foaming (low density) layer 22 is formed for the inside (head), so that the shock absorbing performance upon a second hit on one identical portion is improved.

Industrial Applicability

As described above, according to the helmet of the present invention, since a foam of polyvinylidene chloride is used for the shock absorbing liner, the strain upon molding is small, so that, it is possible to manufacture a liner with a high dimensional accuracy and to provide a helmet easily assembled with the shell.

Further, since the foam of polyvinylidene chloride shows low escape of foaming gas, it has excellent dimensional stability and performance stability for a long period of time, can ensure the performance of the helmet for a long period of time and, particularly, can ensure a degree of freedom in design relative to user's demand. Therefore, since this material has a sufficient strength to be used for racing as well as for ordinary street use, it can be adapted to all types of helmets.

We claim:

1. A helmet having a shell formed by molding of a thermoplastic resin and a shock absorbing liner disposed on inside of the shell, in which the liner is formed of polyvinylidene chloride foam.

2. A helmet as defined in claim 1, wherein said liner comprises a dual layered structure of a high density polyvinylidene chloride foam layer and a low density polyvinylidene chloride foam layer.

3. A helmet as defined in claim 2, wherein said high density polyvinylidene chloride foam layer is in contact with said shell.

* * * * *